(12) United States Patent
Yamanouchi

(10) Patent No.: US 10,036,718 B2
(45) Date of Patent: Jul. 31, 2018

(54) ELECTRODE, COMPOSITE ELECTRODE, AND ANALYZER FOR ANALYZING LIQUID

(71) Applicant: HORIBA, Ltd., Kyoto-shi, Kyoto (JP)

(72) Inventor: Hisashi Yamanouchi, Kyoto (JP)

(73) Assignee: HORIBA, LTD., Kyoto (JP)

( * ) Notice: Subject to any disclaimer, the term of this patent is extended or adjusted under 35 U.S.C. 154(b) by 126 days.

(21) Appl. No.: 15/129,272

(22) PCT Filed: Mar. 31, 2015

(86) PCT No.: PCT/JP2015/060080
§ 371 (c)(1),
(2) Date: Sep. 26, 2016

(87) PCT Pub. No.: WO2015/152219
PCT Pub. Date: Oct. 8, 2015

(65) Prior Publication Data
US 2017/0102351 A1    Apr. 13, 2017

(30) Foreign Application Priority Data
Mar. 31, 2014  (JP) .................................. 2014-074794

(51) Int. Cl.
*G01N 27/333*  (2006.01)
*G01N 27/30*   (2006.01)
*G01N 27/07*   (2006.01)

(52) U.S. Cl.
CPC ......... *G01N 27/333* (2013.01); *G01N 27/301* (2013.01); *G01N 27/302* (2013.01)

(58) Field of Classification Search
CPC .... G01N 27/07; G01N 27/128; G01N 27/226; G01N 27/28; G01N 27/30; G01N 27/301;
(Continued)

(56) References Cited

U.S. PATENT DOCUMENTS 4,053,382 A * 10/1977 Maruyama ............. G01N 27/40
                                                              204/420
2003/0013198 A1    1/2003 Harada
(Continued)

FOREIGN PATENT DOCUMENTS

CN    102265146 A    11/2011
CN    103226032 A     7/2013
(Continued)

OTHER PUBLICATIONS

Extended European Search Report dated Aug. 18, 2017 from the corresponding European Application No. 15773550.7.
(Continued)

*Primary Examiner* — Susan D Leong
(74) *Attorney, Agent, or Firm* — Lucas & Mercanti, LLP

(57) ABSTRACT

A purpose of this invention is to provide an electrode that is extremely preferably used for measuring a pH of a cell culture medium. This electrode is designed to be inserted into an insertion bore arranged on a container into which a sample solution as being a measuring object is put, and comprises an internal electrode, a storage that houses the internal electrode, a gelled or liquefied internal liquid that is filled into the storage so as to contact the internal electrode, and a sensor part that is electrically connected to the internal electrode through the internal liquid and arranged at a distal end surface of the storage as to detect a electric potential of the sample solution. The storage has a positioning surface for positioning the storage at a mounting position at which the inner wall surface of the container and the distal end surface of the storage are on the same plane.

10 Claims, 5 Drawing Sheets

(58) Field of Classification Search
CPC .... G01N 27/302; G01N 27/31; G01N 27/333; G01N 27/40; G01N 27/403; G01N 27/4076
See application file for complete search history.

(56) References Cited

U.S. PATENT DOCUMENTS

2006/0091009 A1* 5/2006 Harman, III ......... G01N 27/333
                                                    204/416
2011/0308946 A1 12/2011 Wilke
2012/0175253 A1 7/2012 Kobayashi

FOREIGN PATENT DOCUMENTS

| DE | 4440580 A1 | 5/1996 |
|----|------------|--------|
| JP | 57-061553 U1 | 9/1955 |
| JP | 59-176952 U1 | 11/1984 |
| JP | 60-079154 U1 | 6/1985 |
| JP | 04-071163 U1 | 6/1992 |
| JP | 2000009676 A | 1/2000 |
| JP | 2002048753 A | 2/2002 |
| JP | 2003028830 A | 1/2003 |
| JP | 2003250708 A | 9/2003 |
| JP | 2007024544 A | 2/2007 |
| JP | 2011220717 A | 11/2011 |

OTHER PUBLICATIONS

International Search Report dated Jun. 23, 2015 for PCT/JP2015/060080 and English translation.
Office Action dated Apr. 11, 2018 from the corresponding Chinese Patent Application No. 201580016722.9 and English translation.

\* cited by examiner

ELECTRODE, COMPOSITE ELECTRODE, AND ANALYZER FOR ANALYZING LIQUID

CROSS REFERENCE TO RELATED APPLICATION

This Application is a 371 of PCT/JP2015/060080 filed on Mar. 31, 2015, which, in turn, claimed the priority of Japanese Patent Application No. JP 2014-074794 filed on Mar. 31, 2014, both applications are incorporated herein by reference.

FIELD OF THE ART

This invention relates to an electrode, a composite electrode and an analyzer for analyzing liquid used for measuring a pH, ORP or a concentration of an ion such as sodium or potassium.

BACKGROUND ART

Conventionally, a pH electrode is used in order to measure a pH of, for example, a sample solution used for an experiment. This pH electrode is inserted into a container in which the sample solution is put and soaked in the sample solution so as to measure the pH of the sample solution, however, an adverse effect might be brought to the experiment because a content of the sample solution attaches to the pH electrode. In addition, in case of cleaning inside of the container, if a distal end part of the pH electrode projects inside of the container, it is necessary to clean the inside of the container carefully in order to prevent breaking the pH electrode. Furthermore, if the distal end part of the pH projects inside of the container, an adhesive material easily attaches to the pH electrode so that a cleaning operation becomes complicated.

In addition, also for a recently conducted regenerative therapy wherein a cell or a part of an organ of a human being or an animal is cultivated and regenerated so as to treat a disease, the pH of a cell culture medium is measured in order to control a cultivation state in case of cultivating the cell. In measuring the pH of the cell cultivation, in case of stirring the cell culture medium, if the cell hits against the electrode, the cell gets stressed and the stress gives a bad influence on the cell cultivation. Then the arrangement of the pH electrode that does not apply stress to the cell is desirable.

For example, the patent document 1 describes a pH electrode that is arranged in a container of a culture medium. The pH electrode is inserted into the container from its side surface to measure a pH of the culture medium. Since a distal end part of the pH electrode projects indie of the container, in case of cleaning the inside of the container, it is necessary to clean the container carefully in order not to break the pH electrode. In addition, there is a problem that an adhesive material easily attaches to the pH electrode so that a cleaning operation becomes complicated. If the culture medium is stirred, there is a problem that the cell hits against the distal end part of the electrode so that the cell gets stressed.

PRIOR ART DOCUMENT

Patent Document

Patent document 1: Japanese Unexamined Utility Model Application Publication No. 60-79154

SUMMARY OF THE INVENTION

Problems to be Solved by the Invention

The present claimed invention intends to solve all of the problems and a main object of this invention is to provide an electrode to which a content of a sample solution does not attach in case of measuring a pH of the sample solution by immerging the electrode into the sample solution in a container and that does not prevent cleaning inside of the container. In addition, this invention is to provide an electrode that can be preferably used for measurement of the pH of, for example, a cell culture medium.

Means to Solve the Problems

More specifically, an electrode in accordance with this invention is an electrode that is inserted into an insertion bore arranged on a container into which a sample solution as being a measuring object is put, and that comprises an internal electrode, a storage that houses the internal electrode, a gelled or liquefied internal liquid that is filled into the storage so as to contact the internal electrode, and a liquid junction or responsive membrane that is electrically connected to the internal electrode through the internal liquid and arranged at a distal end surface of the storage in order to detect a electric potential of the sample solution, and that is characterized by that the storage has a positioning surface for positioning the storage at a mounting position at which the inner wall surface of the container and the distal end surface of the storage are on the same plane.

In accordance with this arrangement, since it is possible to position the storage so that the distal end surface of the storage and the internal wall surface of the container locate on the same plane by means of the positioning surface, if the inside of the container is washed, the electrode can also be cleaned easily, which makes it easy to clean the inside of the container. In addition, this electrode can be preferably used for the measurement of the pH of the cell culture medium. In other words, since the distal end surface of the storage and the internal wall surface are on the same plane, the electrode does not project toward the inside of the container and a step part formed on the container to provide the insertion bore is not exposed. As a result of this, in case that the cell culture medium in the container is stirred, since the cell does not hit against a part of the electrode or the step part, there is no chance that the cell gets stressed. If the cell gets stressed, a bad influence is exerted on cultivation of the cell. However, that is not the case, it becomes possible to measure the pH of the culture medium while conducting cultivation of the cell. In addition, since there is no chance that the cell gets stuck by the projecting composite electrode or the exposed step part, it is possible to measure the pH of the cell culture medium while cultivating the cell by smoothly stirring the cell culture medium.

Furthermore, since the distal end surface of the electrode is formed in a plane shape, even though an amount of the sample solution is small, the sample solution diffuses in the whole of the liquid junction or responsive membrane when the liquid junction or responsive membrane makes contact with the sample solution so that it is possible to measure the pH of the sample solution whose amount is small.

As a concrete embodiment to position the storage at the mounting position represented is an arrangement wherein the storage has an outward surface that faces a direction opposite to the insertion direction, and the storage is positioned at the mounting position when the positioning surface makes an abutting contact with the outward surface.

In addition, the electrode in accordance with this invention is characterized by that the storage comprises a projecting part that projects in a direction that is orthogonal to the insertion direction, and the positioning surface is formed on the projecting part.

In accordance with this arrangement, since the storage is provided with the positioning surface at the projecting part that projects in a direction orthogonal to the insertion direction, in case that the electrode is inserted into the insertion bore of the container, the electrode is stopped to be inserted when the positioning surface makes an abutting contact with the outward surface of the container. With this arrangement, it is possible to position the storage at the mounting position and to arrange the distal end surface of the storage and the internal wall surface of the container on the same plane.

In addition, the electrode in accordance with this invention is characterized by that the storage is fixed to the insertion bore when a ring-shaped member that fits over the projecting part pushes the projecting part against the container.

In accordance with this arrangement, since the ring-shaped member is separately arranged from the storage, it is possible to form the storage smaller compared with a case that the storage comprises the ring-shaped member. As a result of this, the electrode can be downsized in itself so that it is possible to preferably mount this electrode on the insertion bore even though the insertion bore of the container is small.

In addition, the electrode in accordance with this invention is characterized by that the storage is tightly inserted into the insertion bore.

In accordance with this arrangement, since the storage is inserted into the insertion bore without any space there between, it is possible to keep a clean state. In addition, there is no chance that the sample solution such as the cell culture medium enters a space formed between the storage and the insertion bore or the cell gets stuck and accumulates in the space so that it is possible to prevent a bad influence on the cell cultivation.

In addition, the electrode in accordance with this invention is characterized by that the internal electrode is an internal electrode for a reference electrode that measures a reference potential and the internal liquid is an internal liquid for the reference electrode, and the liquid junction is arranged at a distal end surface of the storage.

Furthermore, the electrode in accordance with this invention is characterized by that the internal electrode is an internal electrode for an ion-selective electrode that measures an electric potential of the sample solution and the internal liquid is an internal liquid for the ion-selective electrode, and the responsive membrane is arranged at the distal end surface of the storage.

In addition, a composite electrode in accordance with this invention is a composite electrode that comprises an ion-selective electrode comprising a second internal electrode, a support body that support the second internal electrode, a second internal liquid that is filled in the support body so as to make contact with the second internal electrode, and a responsive membrane that is electrically connected to the second internal electrode through the second internal liquid and that is arranged at the distal end surface of the storage in order to detect the electric potential of the sample solution, and an electrode whose internal electrode and internal liquid are for the reference electrode, and is characterized by that the responsive membrane is arranged on a distal end surface of the support body, and the responsive membrane and the liquid junction are arranged on the same plane.

As a concrete embodiment of the electrode represented is an electrode that is a reference electrode, an ion-selective electrode, or a composite electrode comprising the reference electrode and the ion-selective electrode. Since the reference electrode, the ion-selective electrode or the composite electrode has the above-mentioned arrangement, it is possible to preferably use this electrode for measuring the pH of the cell culture medium.

Furthermore, as a concrete embodiment represented is an analyzer for analyzing liquid that comprises the above-mentioned composite electrode, a conversion device that converts measurement information from the composite electrode into desired information, and a display device that displays the information converted by the conversion device. With using the analyzer for analyzing liquid having the above-mentioned arrangement, since the distal end surface of the composite electrode and the internal wall surface of the container are coplanar, it is possible to obtain the above-mentioned operation and effect.

Effect of the Invention

In accordance with this invention having the above-mentioned arrangement, since the electrode is mounted at the mounting position of the container so as to locate the distal end surface of the electrode and the internal wall surface of the container generally on the same plane, it is possible to keep a clean state. In addition, in case of stirring the cell culture medium, since there is no chance that the cell hits against a part of the projecting electrode or the step part formed for the container to provide the insertion bore and gets stressed, it is possible to measure the pH of the cell culture medium without a bad influence on cultivation of the cell while cultivating the cell.

In addition, since the distal end surface of the electrode and the internal wall surface of the container are generally coplanar, it is possible to clean the inside of the container with ease. Furthermore, since there is no change that the cell gets stuck by the projecting electrode or the exposed step part and the cell accumulates in the projecting electrode or the exposed step part, it is possible to measure the pH of the cell culture medium while cultivating the cell by stilling the cell culture medium smoothly.

Furthermore, since the distal end surface of the electrode is formed in a plane shape, even though the amount of the sample solution is small, the sample solution diffuses in the whole of the liquid junction or responsive membrane when the liquid junction or responsive membrane makes contact with the sample solution so that it is possible to measure the pH of the sample solution.

EXPLANATION OF CODES

Figure 1:
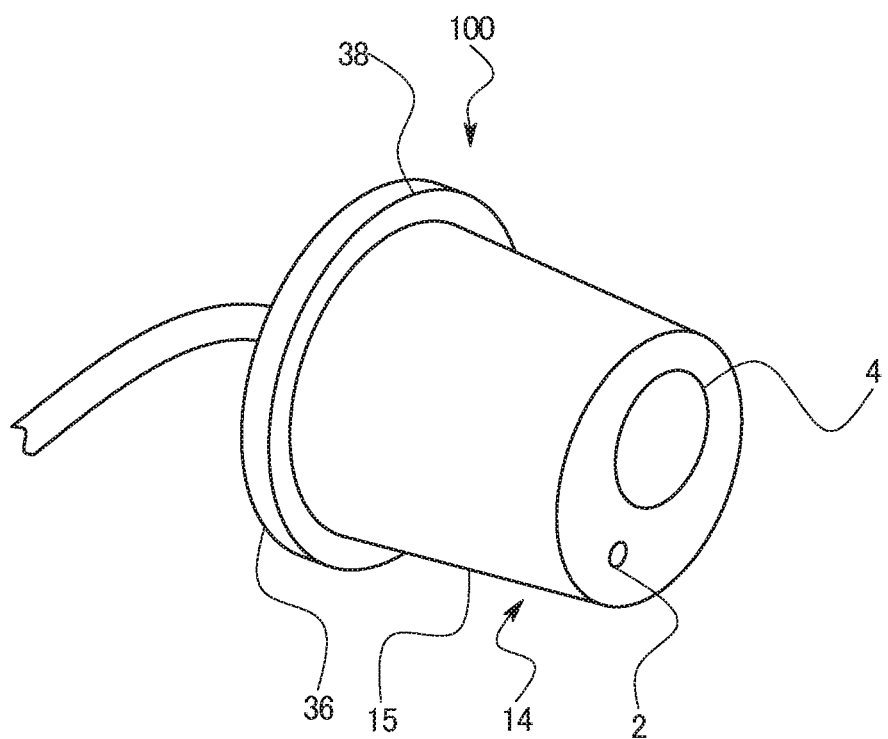
FIG. 1 is a general pattern view of an electrode in accordance with one embodiment of this invention.

100 . . . electrode
2 . . . reference electrode
4 . . . ion-selective electrode
6 . . . composite electrode
10 . . . container
12 . . . insertion bore
14 . . . storage
15 . . . storage body
18 . . . distal end surface
36 . . . cover part
38 . . . projecting part
42 . . . ring-shaped member
72 . . . conversion device
74 . . . display device
200, 300 . . . measurement system
400 . . . analyzer for analyzing liquid

BEST MODES OF EMBODYING THE INVENTION

One embodiment of this invention will be explained with reference to drawings.

Figure 2:
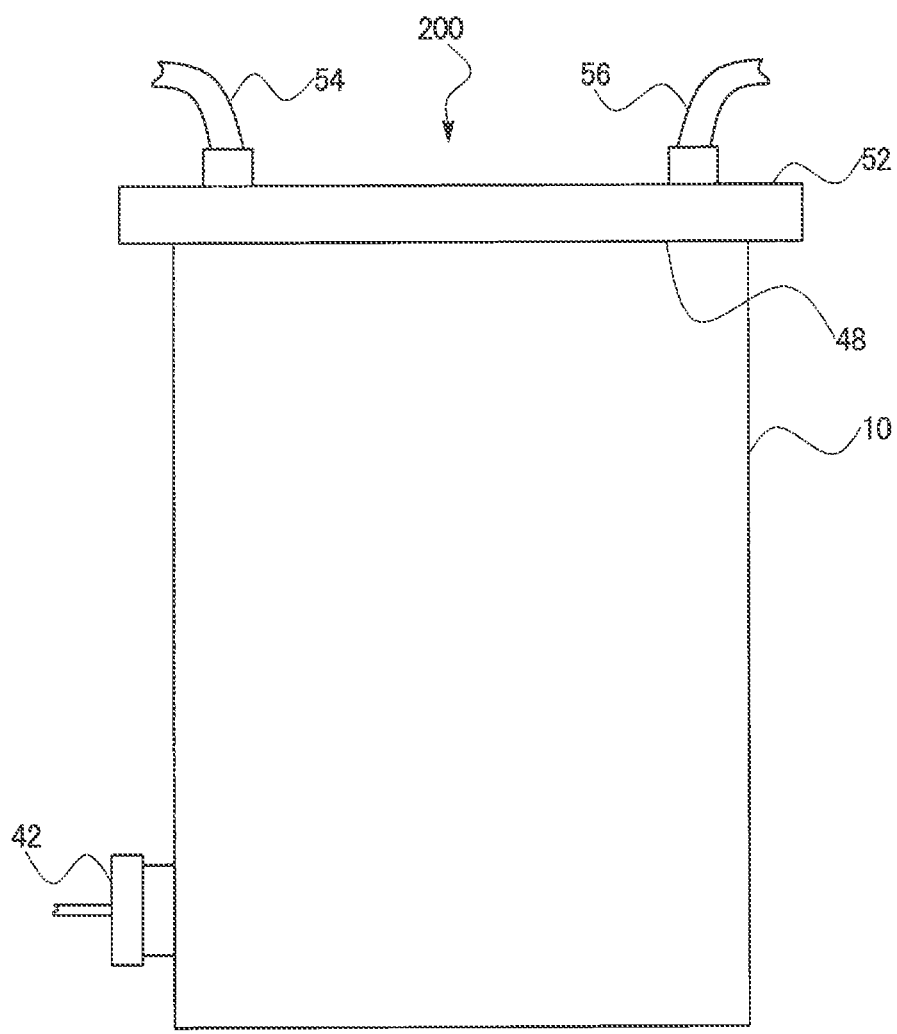
FIG. 2 is a general pattern view of a measurement system in accordance with this embodiment.

An electrode 100 in accordance with this embodiment is shown in FIG. 1. In this embodiment, the electrode 100 is explained as a composite electrode 6 comprising a reference electrode 2 and an ion-selective electrode 4, however, the electrode 100 is not limited to the composite electrode 6 and may be an electrode as the reference electrode 2 or the ion-selective electrode 4. In addition, FIG. 2 and FIG. 3 show a state wherein the electrode 100 is inserted into an insertion bore 12 arranged on a container 100 into which a sample solution 8 as being a measuring object such as, for example, a cell culture medium is contained.

First, the reference electrode 2 will be explained.

Figure 3:
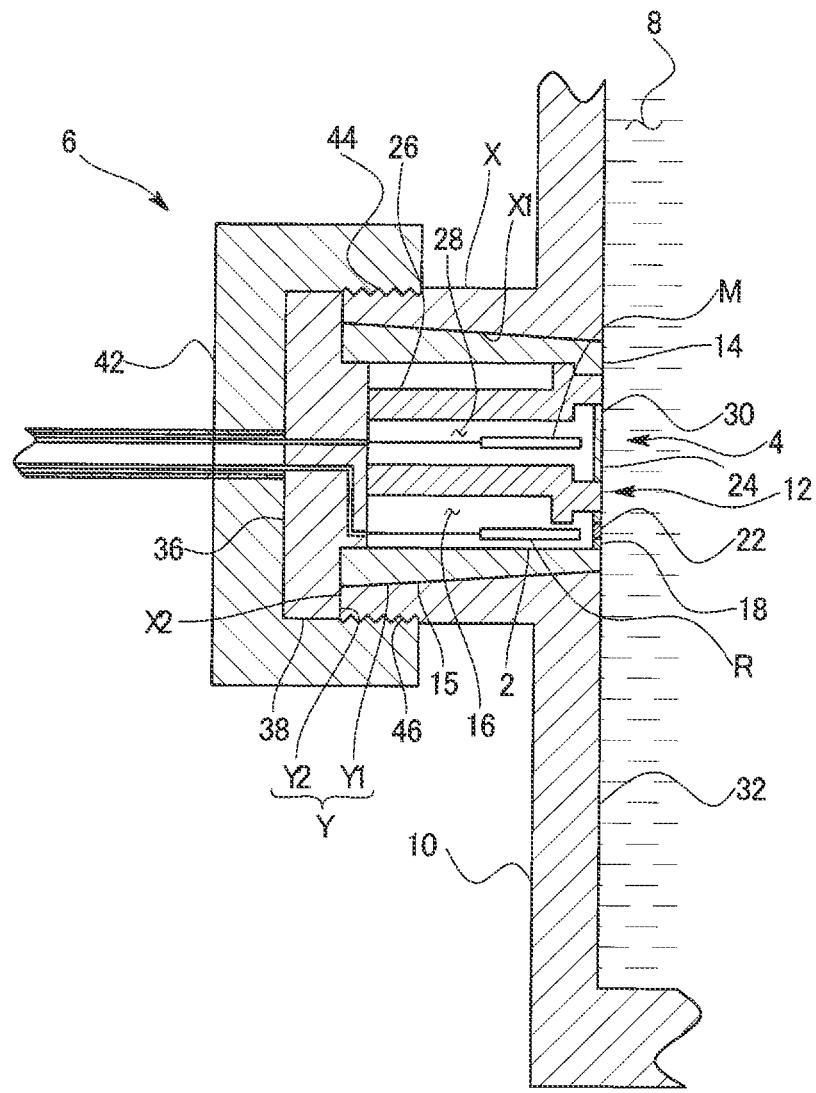
FIG. 3 is an enlarged pattern view of a part of an insertion bore for inserting the electrode of the measurement system in accordance with this embodiment.

The reference electrode 2 comprises, as shown in FIG. 3, an internal electrode (R) for the reference electrode 2, a storage 14 that houses the internal electrode (R), a gelled or liquefied internal liquid 16 for the reference electrode 2 that is filled in the storage 14 so as to contact the internal electrode (R), and a sensor part that is arranged at a distal end surface 18 of the storage 14 and electrically connected to the internal electrode (R) through the internal liquid 16 and that has a liquid junction 22 to detect a reference potential.

Next, the ion-selective electrode 4 will be explained.

The ion-selective electrode 4 comprises, as shown in FIG. 3, a support body 26 having a responsive membrane 24, a second internal liquid 28 for the ion-selective electrode 4 that is filled in the support body 26 and a second internal electrode (M) for the ion-selective electrode 4 that is immersed into the second internal liquid 28. The responsive membrane 24 is arranged at a distal end surface 30 of the support body 26 and an electric potential is measured in accordance with an ionic concentration of the sample solution 8 by means of the responsive membrane 24. The electric potential of the sample solution 8 is a potential difference between the reference electrode 2 and the ion selective electrode 4.

The composite electrode 6 comprise the reference electrode 2 and the ion-selective electrode 4, and the liquid junction 22 of the reference electrode 2 and the responsive membrane 24 of the ion-selective electrode 4 are arranged on a same plane.

More concretely, the composite electrode 6 has the storage 14 to surround the support body 26 and is in a shape of a solid of revolution having the ion-selective electrode 4 and the reference electrode 2 integrally in this embodiment.

The ion-selective electrode 4 is in a cylindrical shape and a planer responsive glass as the responsive membrane 24 is provided on the distal end surface 30 of the support body 26 made of resin. The second internal liquid 28 predetermined for the ion-selective electrode 4 is filled inside of the support body 26, and the second internal electrode (M) comprising a silver/silver chloride electrode is immersed in the second internal liquid 28.

The reference electrode 2 has the cylindrical storage 14 made of resin, similar to the support body 26, to surround an outer peripheral of the support body 26, and a space provided between the support body 26 and the storage 14 is arranged to form an airtightly sealed space.

The cylindrical storage 14 comprises a storage body 15 wherein an opening part is provided at a rear end surface opposed to the distal end surfaces 18, 30, and a cap body 36 that tightly seals the opening part. An outer diameter of the cap body 36 is bigger than an outer diameter of the opening part of the storage body 15, and an outer circumference edge of the cap body 36 becomes a projecting part 38 that projects in a radial direction from the outer peripheral surface of the storage body 15 when the cap body 36 is mounted on the storage body 15. The radial direction is a direction orthogonal to a rotational axis of the storage 14, and a direction orthogonal to a direction (hereinafter also called as an insertion direction) in which the storage 14 is inserted into the insertion bore 12 in this embodiment.

The insertion bore 12 will be explained.

The insertion bore 12 is formed as a part of a container 10 and is an internal space of a mounted part (X) on which a composite electrode 6 is mounted. The mounted part (X) in this embodiment is in a cylindrical shape that projects outside from a side wall of the container 10, and a space surrounded by an inner peripheral surface (X1) of the mounted part (X) is formed as the insertion bore 12. In this embodiment, the inner peripheral surface (X1) of the mounted part (X) is in a tapered shape that gradually reduces its diameter from outside to the inside of the container 10.

In accordance with the above-mentioned arrangement, a step part is formed on the inner wall surface 32 of the container 10 by the inner peripheral surface (X1) of the mounted part (X).

In this embodiment, the storage 14 has a positioning surface (Y) for positioning the storage 14 at a mounting position so as to place the distal end surfaces 18, 30 and the internal wall surface 32 in the same plane.

The positioning surface (Y) is a surface that makes an abutting contact with an outward surface formed on the container 10 and facing a direction opposite to the insertion direction, and is the surface that receives a force whose direction is opposite to the insertion direction from the outward surface when the storage 14 is inserted into the insertion bore 12.

In this embodiment, the inner peripheral surface (X1) of the mounted part (X) and an outer end surface (X2) of the mounted part (X) are formed as the above-mentioned outward surface, and an outer peripheral surface (Y1) of the storage body 15 and an inward surface (Y2) of the projecting part 38 each of which makes an abutting contact with the outward surface respectively are the positioning surface (Y).

More specifically, the storage 14 is positioned at the mounting position when whole of the outer peripheral surface (Y1) tightly attaches to whole of the inner peripheral surface (X1) and the inward surface (Y2) makes an abutting contact with the outer end surface (X2).

The outer peripheral surface (Y1) of the storage body 15 has a shape that corresponds to a shape of the inner peripheral surface (X1) of the mounted part (X) and that is tapered to reduce its diameter gradually from a rear end to a distal end in this embodiment.

As mentioned above, the distal end surfaces 18, 30 of the storage body 14 are placed in the same plane as that of the inner wall surface 32 of the container 10, namely generally coplanar by mounting the storage 14 on the mounting position.

"Generally coplanar" in this embodiment is not necessarily limited to a state wherein the distal end surfaces 18, 30 are strictly coplanar with the inner wall surface 32, and includes a state wherein the distal end surfaces 18, 30 are slightly deviated from the inner wall surface 32 in the insertion direction to an extent that a content (for example, a cell contained in the sample solution 8 as being a cell culture medium) of the sample solution 8 is not obstructed by the above-mentioned step part or the storage 14.

More concretely, it is preferable that the deviation between the distal end surfaces 18, 30 of the storage 14 and the inner wall surface 32 of the container 10 is less than or equal to 5 mm when the storage 14 is mounted at the mounting position. In accordance with this arrangement, the content of the sample solution 8 is difficult to be obstructed by the step so that it is possible to prevent the distal end surfaces 18, 30 from being contaminated. In addition, in case of culturing the sample solution such as a biomedical tissue like a cell or a microorganism, it is preferable that the deviation is less than or equal to 2 mm. This is because if the deviation is more than 2 mm, there is a problem that the cell or the microorganism accumulates in the step part in several weeks after initiation of culturing the cell or the microorganism. If the cell accumulates in the step part, the accumulated cell might grow to be a nucleus so that the cell might differentiate into an untargeted object or the contamination might generate and a problem occurs that a yield drops drastically.

In this embodiment, the composite electrode 6 further comprises a ring-shaped member 42 that fits over the projecting part 38 in order to mount the storage 14 on the above-mentioned mounting position, and the positioning surface (Y) makes an abutting contact with the outward surface by the ring member 24 pushing the projecting part 38 against the container 10 so that the storage 14 is positioned at the mounting position. The ring-shaped member 42 has a screw part 46 that screws to a screw part 44 arranged at the distal end part of the outer peripheral surface of the mounted part (X), and the outer peripheral surface (Y1) of the storage body 15 tightly attaches the inner peripheral surface (X1) of the mounted part (X) and the inward surface (Y2) of the projecting part 38 makes an abutting contact with the outer end surface (X2) of the mounted part (X) so that the storage body 14 is fixed to the insertion bore 12 by screwing the screw parts 44 and 46 each other.

In addition, an opening part (not shown in drawings) for first injecting the internal liquid 16 is arranged on a side wall of the storage part 15, and the storage part 15 is kept in a tightly sealed state by tightly capping the opening part after injecting the internal liquid 16. The internal liquid 16 is a gelled or liquefied KCl solution having a predetermined concentration, and a gelled or liquefied solution is selected in accordance with a measurement condition. A planer liquid junction 22 is arranged on the distal end surface 18 of the storage 14, and the liquid junction 22 is made of a porous body such as, for example, polyethylene, ceramic or Teflon (register trade mark). The internal liquid 16 flows out from the liquid junction 22.

The internal electrode (R) comprising a silver/silver chloride electrode is arranged inside of the storage 14 so as to be immersed in the internal liquid 16. This internal electrode (R) and the second internal electrode (M) of the ion-selective electrode 4 are connected to a potentiometer (not shown in drawings) arranged outside through a wiring respectively, and the pH of the sample solution is measured by this potentiometer. A connecting part between each wiring and the potentiometer is tightly embedded by adhesive or the like so as to secure a sealing property of the tightly sealed space.

The storage 14 is inserted into the insertion bore 12 in a tightly attached state. For example, if a shape of the insertion bore 12 is a column, a shape of the storage 14 is formed to be tightly fit into the column shape of the insertion bore 12. The shape of the insertion bore 12 is not limited to the column, and may be a rectangular parallelepiped as far as the shape of the storage 14 is formed to be tightly fit into the insertion bore 12.

Next, a measurement system 200 comprising the composite electrode 6 will be explained by the use of FIG. 2 and FIG. 3. The measurement system 200 comprises the container 10 into which the sample solution 8 as being the measuring object is placed and the composite electrode 6 having the reference electrode 2 and the ion-selective electrode 4 each of which is mounted on the insertion bore 12 of the container 10 so as to immerse the liquid junction 22 and the responsive membrane 24 in the sample solution 8. Although not shown in drawings, the composite electrode 6 is connected to the potentiometer and a recording device arranged outside and the pH of the sample solution 8 is measured by the potentiometer and the pH value is recorded by the recording device.

More concretely, the measurement system 200 comprises the container 10 having an opening part 48 on its upper part. The container 10 is especially preferably used for culturing a cell, and may be made of resin as far as a function as the material of the container 10 is not damaged due to sterilization. In addition, if the container 10 is made of glass, it is possible to restrain degradation of the material due to radiation sterilization such as gamma-radiation. It is a matter of course that the container 10 can be used also for the sample solution other than the cell culture medium. In addition, an impeller (not shown in drawings) to stir the sample solution 8 is provided in the container 10 in a state of extending upward from a bottom part of the container 10. A rotation axis such as a motor, now shown in drawings, is inserted into a bottom part of the impeller so that the sample solution 8 is stirred by the impeller rotated by a rotational movement of the rotation axis.

Furthermore, a cap member 52 is arranged at the opening part 48 of the container 10 so as to make it possible to keep the container 10 in a tightly sealed state. The cap member 52 is provided with tubes 54, 56 arranged with its distal end part penetrating the cap member 52, and the sample solution 8 such as the cell culture medium flows in the container 10 from the tube 54 and a buffer solution or the like that is necessary for cultivating the cell flows in from the tube 56. A space between the tube 54, 56 and the cap member 52 is tightly sealed by, for example, an adhesive or the like.

In case of measuring the pH of the sample solution 8 such as the cell culture medium by the use of this measurement system 200, the cell culture medium is heated to a temperature, for example, at about 30 degrees Celsius~50 degrees Celsius, suitable for cultivation. Then, the cell is cultivated while the impeller in the container 10 stirs the cell culture medium and the pH of the cell culture medium is measured by the composite electrode 6 mounted on the side surface of the container 10.

Figure 4:
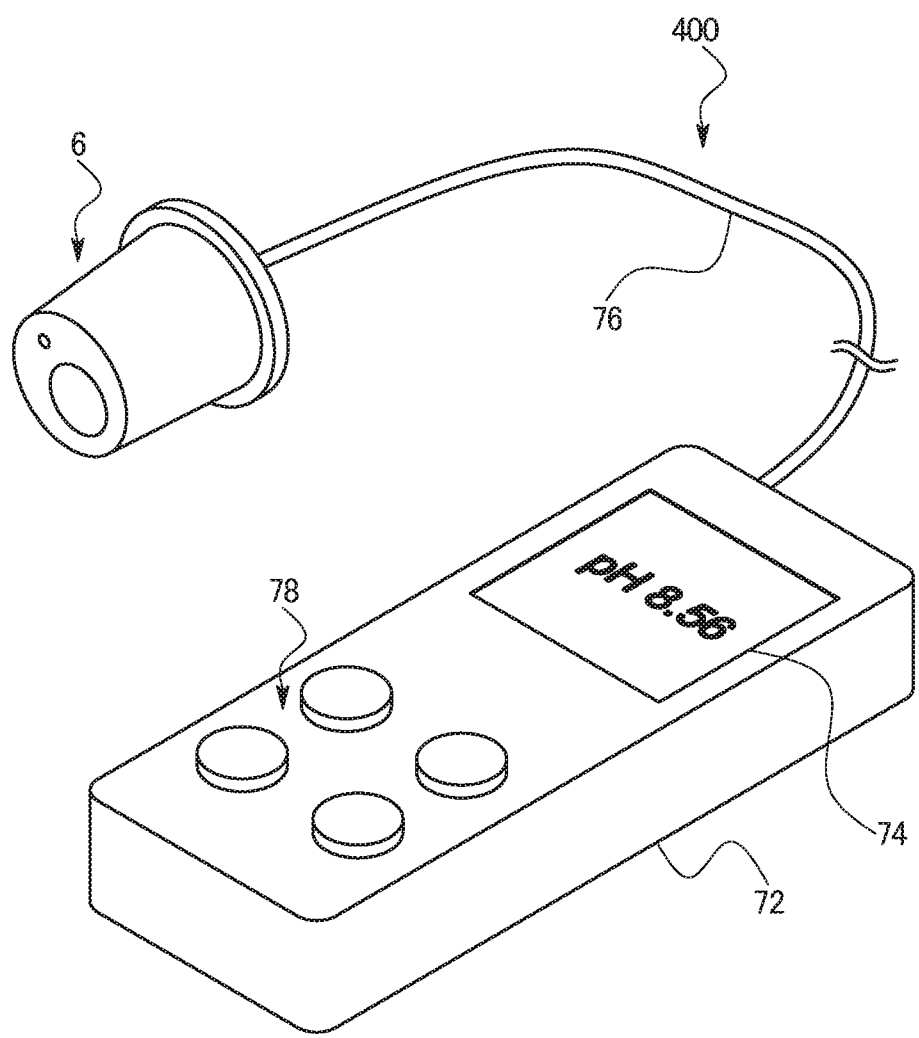
FIG. 4 is a general pattern view of an analyzer for analyzing liquid in accordance with this embodiment.

Next, an analyzer for analyzing liquid 400 comprising the composite electrode 6 will be explained with reference to FIG. 4. The analyzer for analyzing liquid 400 comprises the composite electrode 6, a conversion device 72 that converts measurement information from the composite electrode 6 into desired information and a display device 74 that displays the information converted by the conversion device 72. Concretely, the composite electrode 6 and the conversion device 72 are connected by a signal cable 76 having a predetermined length. The signal cable 76 transfers a electric potential of the sample solution 8 such as the cell culture medium detected by the composite electrode 6 to the conversion device 72 comprising an arithmetic processing unit, and the transferred electric potential is converted to a desired data such as the pH value by the conversion device 72. The data such as the pH value is displayed on the display device 74 such as a liquid crystal display so that it is possible for an operator to verify the pH value of the sample solution 8.

When using this analyzer for analyzing liquid 400, multiple buttons 78 arranged for the conversion device 72 are operated. Each function, for example, correction, initiation of the measurement or termination of the measurement, is allocated to each of the buttons 78 respectively. The measurement of the pH of the sample solution 8 is initiated by pushing the initiation of the measurement button, and the measurement of the pH is terminated by pushing the termination of the measurement button.

When the composite electrode 6 of the analyzer for analyzing liquid 400 having the above-mentioned arrangement is set into the insertion bore 12 of the container 10, it is possible to measure the pH of the cell culture medium without applying any stress to the cell while cultivating the cell.

In this embodiment, the conversion device 72 and the display device 74 are arranged separately from the composite electrode 6, however, it is not limited to this and the conversion device 72 may be downsized and arranged inside of the composite electrode 6 and only the display device 74 may be arranged outside of the composite electrode 6. Furthermore, the display device 74 may also be integrally formed with the composite electrode 6. In accordance with this arrangement, it is possible to downsize the analyzer for analyzing liquid 400 itself and simplify the structure of the measurement system 200.

Since the composite electrode 6 has the above-mentioned arrangement, it is possible to preferably use this composite electrode 6 for measuring the pH of the cell culture medium. More specifically, since the composite electrode 6 and the container 10 are so placed that the internal wall surface 32 of the container 10 and the distal end surfaces 18, 30 of the composite electrode 6 are generally coplanar, there is no chance that the composite electrode 6 projects in the container 10 and the step part formed to provide the container 10 with the insertion bore 12 is exposed. As a result of this, in case that the cell culture medium in the container 10 is stirred, there is no chance that the cell touches the composite electrode 6 so that the cell is not stressed. If the cell is stressed, a bad influence is exerted on cultivation, however, with this arrangement, the cell is not stressed so that it is possible to measure the pH of the cell culture medium while the cell is cultivated.

The reference electrode 2 and the ion-selective electrode 4 are made of resin in this embodiment, however, they may be made of other material as far as the material can sterilize without causing harmful effect on cell cultivation and the function as the composite electrode 6 is not lost due to deterioration of the material because of sterilization. For example, in case the material is glass, it is possible to suppress degradation of the material because of sterilization by radiation such as gamma rays and to keep the function as the composite electrode 6.

In addition, since there is no chance that the cell gets stuck by the projecting composite electrode 6 or the exposed step part, it is possible to measure the pH of the cell culture medium while cultivating the cell by smoothly stirring the cell culture medium. Furthermore, since the distal end surfaces 18, 30 and the inner wall surface 32 of the container 10 are generally coplanar, it is possible to wash inside of the container 10 easily. This composite electrode 6 can be used also for measuring the pH of the sample solution other than the cell culture medium.

Furthermore, since the distal end surfaces 18, 30 of the composite electrode 6 are formed in a plane shape, even though an amount of the sample solution 8 is small, the sample solution 8 diffuses in the whole of the sensor part when the sensor part having the liquid junction 22 and the responsive membrane 24 makes contact with the sample solution 8 so that it is possible to measure the pH of the sample solution 8 whose amount is small.

In addition, in case that the composite electrode 6 is inserted into the insertion bore 12, since the outer peripheral surface (Y1) of the storage body 15 is tightly attached to the inner peripheral surface (X1) of the mounted part (X) and the inward surface (Y2) of the projecting part 38 makes an abutting contact with the outer end surface (X2) of the mounted part (X), insertion of the composite electrode 6 stops at this position so that the distal end surfaces 18, 30 of the storage 14 and the inner wall surface 32 of the container 10 are generally coplanar.

The projecting part 38 should project so as to make an abutting contact with the outside end surface (X2) of the mounted part (X), and at least a part of the projecting part 38 may project in a radial direction or the projecting part 38 may have a shape of a toothed gear so as to make an abutting contact partially with the outer end surface (X2). Furthermore, the projecting part 38 may have a tapered shape, and the composite electrode 6 is mounted at the mounting position by making the tapered shape part abutting contact with the outer end surface (X2) of the mounted part (X).

Furthermore, the storage 14 in this embodiment has the outer peripheral surface (Y1) of the storage body 15 and the inward surface (Y2) of the projecting part 38 as the positioning surface (Y), however, the storage 14 may have either one of them.

More concretely, in case that, for example, the cap part 36 has no projecting part 38, the storage 14 has only the outer peripheral surface (Y1) of the storage body 15 as the positioning surface (Y).

Meanwhile, in case that the inner peripheral surface (X1) of the mounted part (X) and the outer peripheral surface (Y1) of the storage body 15 have no tapered surface and no force is applied to the outer peripheral surface (Y1) in a direction opposite to the insertion direction, the storage 14 has only an inward surface (Y2) of the projecting part 38 as the positioning surface (Y).

It is a matter of course that the storage 14 may further have one or multiple positioning surfaces in addition to two positioning surfaces (Y) in the above-mentioned embodiment.

In addition, the storage 14 is fixed to the insertion bore 12 by helically connecting a screw part 44 of the mounted part (X) with a screw part 46 of the ring-shaped member 42 in the above-mentioned embodiment, however a part or all or the positioning surface (Y) may be fixed to the mounted part (X) by, for example, heat sealing.

In accordance with the above-mentioned arrangement, it is preferable that a part or all of the positioning surface (Y) is made of the same material, and more concretely, the positioning surface (Y) is preferably made of resin such as, for example, polyethylene.

As a more specific embodiment represented is an arrangement wherein either one or both of the outer peripheral surface (Y1) of the storage body 15 and the inner peripheral surface (X1) of the mounted part (X), and the inward surface (Y2) of the projecting part 38 and the outward surface (X2) of the mounted part (X) is fixed by heat sealing.

In addition, in the above-mentioned embodiment, the force whose direction is opposite to the insertion direction is applied to the positioning surface (Y) by making the positioning surface (Y) abutting contact with the container 10, however, the arrangement may be so that a frictional force generates between the outer peripheral surface (Y1) of the storage body 15 and the inner peripheral surface (X1) of the mounted part (X) and the frictional force applies to the outer peripheral surface (Y1) of the storage body 15 as a force whose direction is opposite to the insertion direction.

Concretely, the frictional force surface should be formed on the outer peripheral surface (Y1) of the storage body 15 and the inner peripheral surface (X1) of the mounted part (X) so that the above-mentioned frictional force generates at the mounting position where the distal end surfaces 18, 30 of the storage 14 and the internal wall surface 32 of the container 10 locate on the same plane.

In accordance with this arrangement, the storage 14 can be fixed to the mounting position securely by fittingly inserting the cap member made of rubber in the storage 14 from outside in a state that the storage 14 is mounted at the mounting position.

In addition, the storage 14 may be fixed to the cap member by fixing the cap member in a state that an adhesive is applied to a rear surface of the cap member and by drawing the storage 14 toward the cap member together with a signal cable 76.

In accordance with this arrangement, there is no need of forming a frictional surface and it is possible to fix the storage 14 at the mounting position.

In addition, since the composite electrode 6 has the ring-shaped member 42 having the above-mentioned arrangement, it is possible to provide the ring-shaped member 42 separately from the storage 14 so that the storage 14 can be downsized compared with an arrangement wherein the storage 14 comprises the ring-shaped member 42. As a result of this, it is possible to downsize the composite electrode 6 in itself so that the composite electrode 6 can be preferably mounted on the insertion bore 12 of the container 10 even though the insertion bore 12 is small.

The composite electrode 6 may be mounted on the mounting position by providing the ring-shaped member 42 with a flange part that projects in the radial direction along a peripheral part and by fixing the flange part to the container 10 by a screw member or the like.

In addition, since the storage 14 is tightly inserted into the insertion bore 12, in other words, the storage 14 is inserted into the insertion bore 12 without any space therebetween, there is no chance that the sample solution such as the cell culture medium enters a space formed between the storage 14 and the insertion bore 12 or the cell gets stuck and accumulates in the space so that it is possible to prevent a bad influence on the cell cultivation. An external form of the storage 14 may be a truncated cone, or may be a various shape such as a columnar shape or a rectangular parallelepiped shape as far as it can be tightly inserted into the insertion bore 12.

Since the storage 14 forms a closed space, if the reference electrode 2 is once sterilized, the sterilized state can be kept. As a result of this, in case that the cell cultivation is conducted, for example, for several weeks to several months, there is no fear that bacteria enters inside of the reference electrode 2 from outside so that it is possible to previously prevent an adverse effect on the cell cultivation.

Since a closed space is formed for the storage 14 by the cover part 36, if the composite electrode 6 is once sterilized, the sterilized state can be kept. As a result of this, there is no fear that bacteria enters inside of the composite electrode 6 from outside during measurement of the pH of the cell culture medium so that it is possible to previously prevent an adverse effect on the cell cultivation.

The composite electrode 6 has been explained, however, the electrode 100 may be the reference electrode 2 or the ion-selective electrode 4. In case that the electrode 100 is the reference electrode 2, the internal electrode and the internal liquid for the reference electrode are used, and the liquid junction made of a porous material such as polyethylene is provided for the sensor part. In addition, in case that the electrode 100 is the ion-selective electrode 4, the internal electrode and the internal liquid for the ion-selective electrode are used, and the planar glass responsive membrane is provided as the responsive membrane for the sensor part. in this invention, if the gamma ray is irradiated on the glass responsive membrane, a drift amount of the response value (measured value) is less compared with the ion sensor such as ISFET, then it has been cleared that it is possible for the glass responsive membrane to conduct a measurement with high accuracy especially for a usage that requires sterilization.

Figure 5:
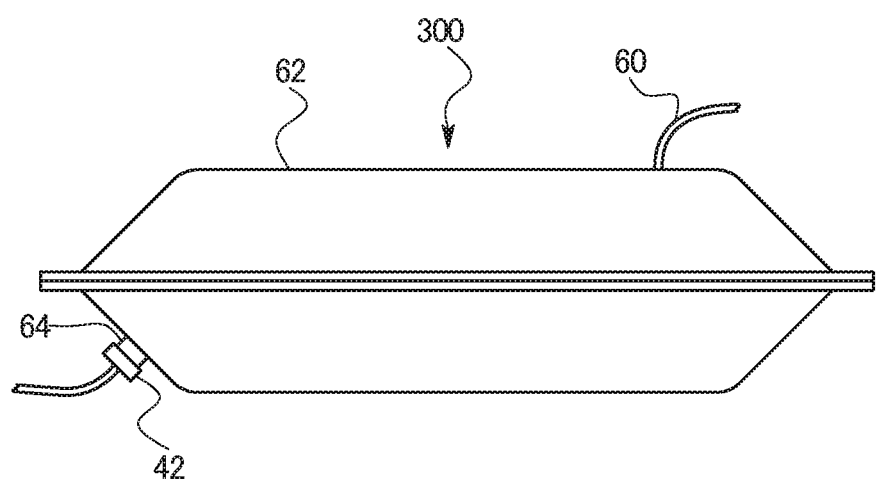
FIG. 5 is a general pattern view of a measurement system in accordance with another embodiment of this invention.

Next, a measurement system 300 in accordance with other embodiment using the composite electrode 6 will be explained with reference to FIG. 5. A container 62, into which a sample solution 8 is put, of this measurement system 300 is formed in a bag-shape made of resin. The bag-shaped container 62 has durability so as not to leak the cell culture medium even though the cell cultivation is conducted for several weeks to several months with the cell culture medium put into the container 62. It is a matter of course that the container 62 can be used also for a sample solution other than the cell culture medium. An insertion bore 64 into which the composite electrode 6 is inserted is so formed that the internal wall surface of the container 62 becomes generally flat with the distal end surfaces 18, 30 of the composite electrode 6. Although not shown in drawings, the composite electrode 6 is connected to a potentiometer and a recording device provided outside, and the pH of the cell culture medium is measured by the potentiometer and the measured pH value is recorded by the recording device.

A tube 60 is provided on an upper surface of the container 62 in a manner that a distal end part of the tube 60 penetrates the container 62 so as to be in communication with inside of the container 62, and the sample solution 8 such as the cell culture medium or a buffer solution necessary for cultivation of the cell flows in the container 62 through the tube 60. The tube 60 is tightly attached to the container 62 by an adhesive or the like. The cell culture medium is stirred by, for example, shaking the container 62.

In accordance with the measurement system 300 having the above-mentioned arrangement, since the distal end surfaces 18, 30 of the composite electrode are formed to be generally flat to the internal wall surface of the container 62, it is easy to clean inside of the container 62 so that the container 62 can be kept clean. In addition, in case of stirring the cell culture medium, it is possible to prevent the bad influence on the cell cultivation caused by the cell that collides with the composite electrode 6 and gets stressed.

In addition, since the insertion bore of the composite electrode 6 has the above-mentioned arrangement, it is possible to place the bag-shaped container 62 at any part even though the container 62 has any shape. Then, since there is no limitation for an installation site of the composite electrode 6, it is possible to install the composite electrode 6 at a desired place intended for the measurement of the pH.

Also for the measurement system 300, the electrode 100 may be the reference electrode 2 or the ion-selective electrode 4.

The electrode in accordance with this invention can be used in various fields.

For example, if an insertion bore is arranged on a pipe used for various processes and the electrode in accordance with this invention is inserted into this insertion bore, it is possible to measure the pH of sewage or tap water flowing in the pipe.

In addition, in case of cultivating biological tissue such as microorganism in a culture medium housed in a dish, if an insertion bore is provided on side wall of the dish and the electrode in accordance with this invention is inserted into the insertion bore, it is possible to measure the pH of the culture medium without interfering monitoring the microorganism by a microscope.

In addition, it is a matter of course that the present claimed invention is not limited to the above-mentioned embodiment and may be variously modified without departing from a spirit of the invention.

POSSIBLE APPLICATIONS IN INDUSTRY

In accordance with this invention, it is possible to provide an electrode that can be extremely preferably used for measuring a pH of a cell culture medium.

The invention claimed is:

1. An electrode that is inserted into an insertion bore arranged on a container into which a sample solution as being a measuring object is put, and is characterized by comprising
    an internal electrode,
    a storage that houses the internal electrode,
    a gelled or liquefied internal liquid that is filled into the storage so as to contact the internal electrode, and
    a liquid junction or responsive membrane that is electrically connected to the internal electrode through the internal liquid and arranged at a distal end surface of the storage in order to detect an electric potential of the sample solution, wherein
    the storage has a positioning surface for positioning the storage at a mounting position at which the inner wall surface of the container and the distal end surface of the storage are on the same plane.

2. The electrode described in claim 1, wherein
the storage is positioned at the mounting position when the positioning surface receives a force whose direction is opposite to an insertion direction of the storage inserted into the insertion bore.

3. The electrode described in claim 2, wherein
the storage has an outward surface that faces a direction opposite to the insertion direction, and
the storage is positioned at the mounting position when the positioning surface makes an abutting contact with the outward surface.

4. The electrode described in claim 2, wherein
the storage comprises a projecting part that projects in a direction that is orthogonal to the insertion direction, and
the positioning surface is formed on the projecting part.

5. The electrode described in claim 4, wherein
the storage is fixed to the insertion bore when a ring-shaped member that fits over the projecting part pushes the projecting part against the container.

6. The electrode described in claim 1, wherein
the storage is tightly inserted into the insertion bore.

7. The electrode described in claim 1, wherein
the internal electrode is an internal electrode for a reference electrode and the internal liquid is an internal liquid for the reference electrode, and the liquid junction is arranged at the distal end surface of the storage.

8. The electrode described in claim 1, wherein
the internal electrode is an internal electrode for an ion-selective electrode and the internal liquid is an internal liquid for the ion-selective electrode, and the responsive membrane is arranged at the distal end surface of the storage.

9. A composite electrode comprising
an ion-selective electrode having
    a second internal electrode,
    a support body that supports the second internal electrode,
    a second internal liquid that is filled in the support body so as to make contact with the second internal electrode, and
    a responsive membrane that is electrically connected to the second internal electrode through the second internal liquid and that is arranged at a distal end surface of the support body in order to detect an electric potential of the sample solution, and
the electrode described in claim 7, and wherein
the responsive membrane and the liquid junction are arranged on the same plane.

10. An analyzer for analyzing liquid comprising
the composite electrode described in claim 9,
a conversion device that converts measurement information from the composite electrode into desired information, and
a display device that displays the information converted by the conversion device.

* * * * *